(12) United States Patent  (10) Patent No.: US 8,840,657 B2
Hartley  (45) Date of Patent: Sep. 23, 2014

(54) SELF EXPANDING STENT

(75) Inventor: David Ernest Hartley, Subiaco (AU)

(73) Assignee: Cook Medical Technologies LLC, Bloomington, IN (US)

( * ) Notice: Subject to any disclaimer, the term of this patent is extended or adjusted under 35 U.S.C. 154(b) by 1154 days.

(21) Appl. No.: 11/654,423

(22) Filed: Jan. 17, 2007

(65) Prior Publication Data

US 2007/0191922 A1  Aug. 16, 2007

Related U.S. Application Data

(60) Provisional application No. 60/759,851, filed on Jan. 18, 2006.

(51) Int. Cl.
A61F 2/06 (2013.01)
A61F 2/86 (2013.01)
A61F 2/89 (2013.01)
A61F 2/07 (2013.01)

(52) U.S. Cl.
CPC ........... *A61F 2/86* (2013.01); *A61F 2220/0075* (2013.01); *A61F 2002/075* (2013.01); *A61F 2/89* (2013.01); *A61F 2/07* (2013.01); *A61F 2002/067* (2013.01)
USPC ........................................ 623/1.13; 623/1.15

(58) Field of Classification Search
USPC ............... 623/1.15, 1.11, 1.12, 1.13, 1.16
See application file for complete search history.

(56) References Cited

U.S. PATENT DOCUMENTS

| | | | | |
|---|---|---|---|---|
| 5,035,706 A | * | 7/1991 | Giantureo et al. | 606/198 |
| 5,133,732 A | | 7/1992 | Wiktor | |
| 5,314,444 A | | 5/1994 | Gianturco | |
| 5,451,235 A | * | 9/1995 | Lock et al. | 606/213 |
| 7,399,314 B2 | * | 7/2008 | Butaric et al. | 623/1.13 |
| 2001/0039450 A1 | * | 11/2001 | Pavcnik et al. | 623/1.24 |
| 2003/0125795 A1 | * | 7/2003 | Pavcnik et al. | 623/1.13 |
| 2003/0191521 A1 | | 10/2003 | Denardo | |
| 2003/0199967 A1 | * | 10/2003 | Hartley et al. | 623/1.13 |
| 2004/0117004 A1 | * | 6/2004 | Osborne et al. | 623/1.36 |
| 2004/0122504 A1 | | 6/2004 | Hogendijk | |
| 2004/0147997 A1 | * | 7/2004 | Gittings | 623/1.11 |
| 2004/0167619 A1 | * | 8/2004 | Case et al. | 623/1.34 |
| 2004/0176833 A1 | * | 9/2004 | Pavcnik et al. | 623/1.13 |
| 2004/0186558 A1 | * | 9/2004 | Pavcnik et al. | 623/1.24 |
| 2004/0210301 A1 | * | 10/2004 | Obermiller | 623/1.24 |
| 2005/0143807 A1 | * | 6/2005 | Pavcnik et al. | 623/1.24 |
| 2005/0171598 A1 | * | 8/2005 | Schaeffer | 623/1.35 |
| 2005/0177222 A1 | * | 8/2005 | Mead | 623/1.13 |

FOREIGN PATENT DOCUMENTS

EP     0997115    5/2000
WO     WO 98/27894    7/1998

* cited by examiner

*Primary Examiner* — David Eastwood
(74) *Attorney, Agent, or Firm* — Richard J. Godlewski

(57) ABSTRACT

A self expanding stent (10) formed from a resilient wire. The resilient wire comprises a zig zag form including an odd number of struts (12) such as seven struts and a bend (14) between each strut. There is first loop (18) of the resilient wire at the terminal end of a first strut and a second loop (18) of the resilient wire at the terminal end of a last strut. The stent as formed is substantially planar but in use is formed into a substantially cylindrical form (20) by being stitched onto a tubular body of a biocompatible graft material with at least the first strut and the last strut overlapping.

10 Claims, 3 Drawing Sheets

SELF EXPANDING STENT

CROSS-REFERENCE TO RELATED APPLICATIONS

This application claims priority of provisional application Ser. No. 60/759,851, filed Jan. 18, 2006.

TECHNICAL FIELD

This invention relates to a stent and more particularly to a self expanding stent used in endovascular therapies.

BACKGROUND OF THE INVENTION

Self expanding stents are used either bare or in conjunction with a biocompatible graft material in endovascular therapies in which the stent is placed in a body lumen to reinforce the lumen or a tubular graft placed into the lumen.

Self expanding stents are generally formed from a resilient wire such as Nitinol™ or stainless steel and made in a zig-zag form with the ends joined to form a cylindrical or polygonal body. The cylindrical or polygonal body can be reduced in diameter by compressing the stent against its resilient forces to permit placement by endovascular techniques and then released to expand in a desired position in the vasculature. The joining of the ends of the resilient wire can be a problem because joining requires welding or soldering and the heating involved can induce brittleness around the joint.

Nitinol™ in particular, is difficult to join and the region around the joint may need to be annealed which could remove the resilient nature of the material. This invention proposes an alternative method of forming self expanding stents and a stent so formed or at least provides a practitioner with a useful alternative.

Throughout this specification the term distal with respect to a portion of the aorta, a deployment device or a prosthesis is the end of the aorta, deployment device or prosthesis further away in the direction of blood flow away from the heart and the term proximal means the portion of the aorta, deployment device or end of the prosthesis nearer to the heart. When applied to other vessels similar terms such as caudal and cranial should be understood.

SUMMARY OF THE INVENTION

In one form therefore the invention is said to reside in a self expanding stent comprising a resilient wire, the resilient wire comprising a plurality of struts and a bend between each strut, the stent as formed being substantially planar and in use being able to be formed into a substantially cylindrical form with at least the first strut and the last strut overlapping.

Preferably the self expanding stent comprises a first loop of the resilient wire at the terminal end of the first strut and a second loop of the resilient wire at the terminal end of the final strut. The loops preferably comprise at least one and a quarter turns of the resilient wire.

There may be an odd number of struts such as the stent comprising seven struts and six bends.

Alternatively there can be an even number of struts and at least two struts overlapping when the stent is formed into the substantially cylindrical form.

The resilient wire can be selected from the group comprising Nitinol™, stainless steel, cobalt alloys and titanium alloys.

The stent is formed into its cylindrical form by being stitched onto a tubular body of a biocompatible graft material with at least the first strut and the last strut overlapping.

In an alternative form the invention resides in a self expanding stent comprising a resilient wire, the resilient wire comprising a zig zag form including plurality of struts and a plurality of bends, a bend between each strut, a first loop of the resilient wire at the terminal end of the first strut and a second loop of the resilient wire at the terminal end of the last strut, the stent in use being able to be formed into a substantially cylindrical form with the first strut and the last strut overlapping.

In an alternative form the invention resides in a self expanding stent comprising a resilient wire, the resilient nitinol wire comprising a zig zag form including seven struts and a bend between each strut, a first loop of the resilient wire at the terminal end of a first strut and a second loop of the resilient wire at the terminal end of a last strut, the stent in use being formed into a substantially cylindrical form by being stitched onto a tubular body of a biocompatible graft material with at least the first strut and the last strut overlapping.

It will be seen that by this invention there is provided a self expanding stent which when mounted onto a tubular body of graft material can be made into the desirable cylindrical form but does not have any welded joint which reduces the chance of fracture caused by embrittlement which may occur during welding or soldering. This is particularly desirable for Nitinol™ wire.

BRIEF DESCRIPTION OF THE DRAWING

This then generally describes the invention but to assist with understanding reference will now be made to the accompanying drawings which show various embodiments of the invention.

In the Drawings.

DETAILED DESCRIPTION

Figure 1:
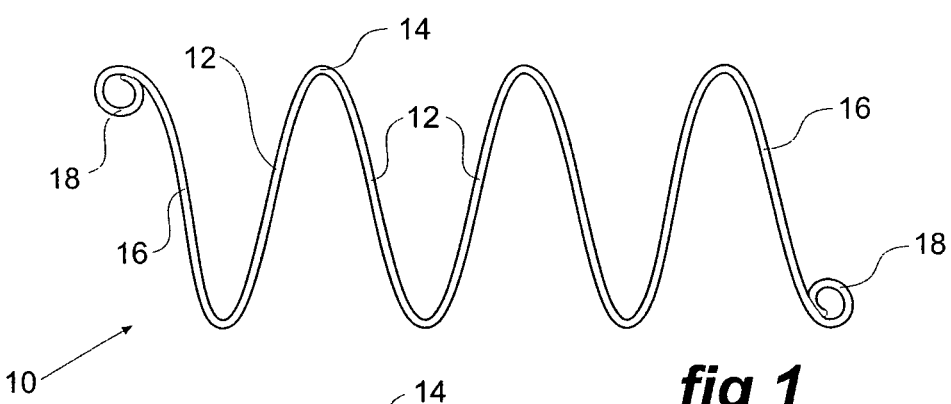
FIG. 1 shows one form of stent as formed according to the present invention.
Figure 2:
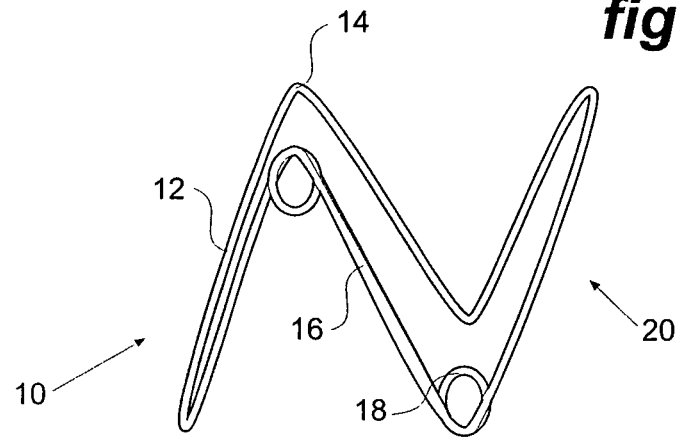
FIG. 2 shows a perspective view the embodiment of FIG. 1 formed into a cylindrical self expanding stent.
Figure 3:
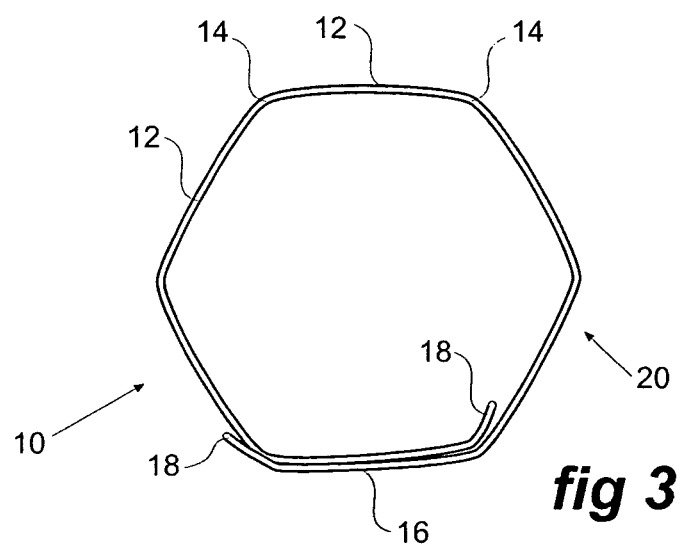
FIG. 3 shows a plan view of the embodiment of FIG. 2.

Now looking at the drawings and more particularly the first embodiment of stent according to the present invention shown in FIGS. 1 to 3.

The stent 10 is formed from a resilient wire such as Nitinol™ wire or stainless steel and comprises a plurality of struts 12 with a bend 14 between each pair of struts 12. In this embodiment there are seven struts 12 and six bends 14 between them. The terminal struts 16 at each end terminate in a loop 18 which comprises at least one turn of the resilient wire and preferably one and a quarter turns. The use of the loops 18 prevent sharp ends from the wire stent from digging into the vasculature into which a stent graft, incorporating the self expanding stent of the present invention, is deployed. As formed the struts, bends and loops are in a single plane and when they are to be used they are formed into a cylindrical or polygonal body 20 as shown in FIG. 2. In the cylindrical form the terminal struts 16 overlap each other to give in effect an at least one strut overlap. When there are an odd number of struts then the terminal loops 18 are positioned at the opposite ends of the cylindrical or polygonal body 20.

The embodiment shown in FIGS. 1 to 3 has seven struts 12 and six bends 14 between them and hence when formed into cylindrical or polygonal body 20 has a plan view in the shape of a hexagon as can be seen in FIG. 3.

When assembled onto a stent graft the stent is maintained into its cylindrical or polygonal body form by being stitched to the tubular body of the graft material.

Nitinol™ is a shape memory metal formed from a nickel-titanium (NiTi) alloy that "remembers" its geometry. The wire is formed into the desired zig-zag shape and then heat treated to retain that shape. After cooling, if it is deformed, it will return to the desired zig-zag shape.

Figure 4:
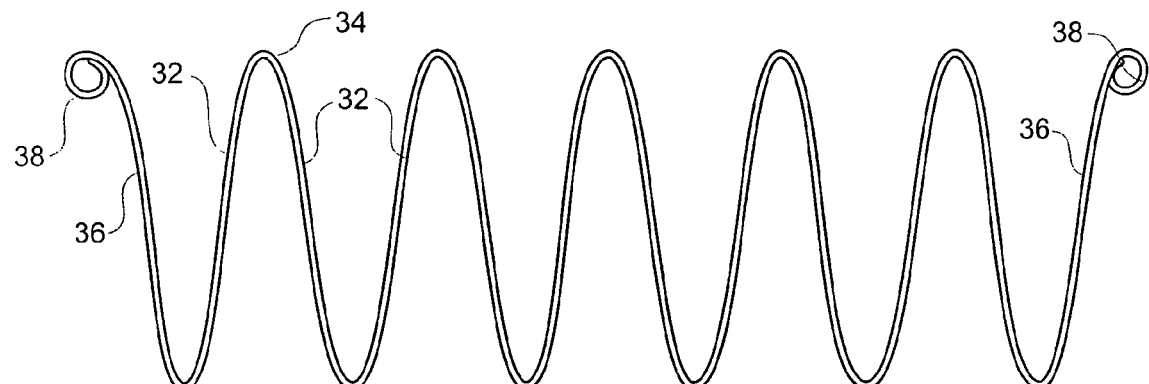
FIG. 4 shows an alternative form of stent as formed according to the present invention.
Figure 5:
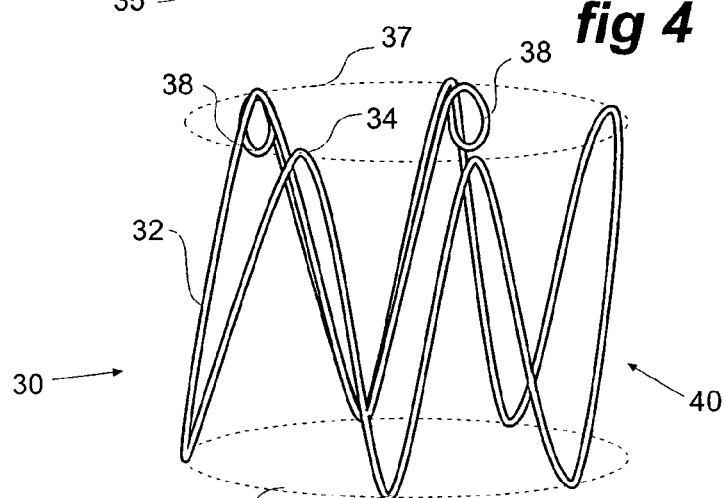
FIG. 5 shows a perspective view of the embodiment of FIG. 4 formed into a cylindrical self expanding stent.
Figure 6:
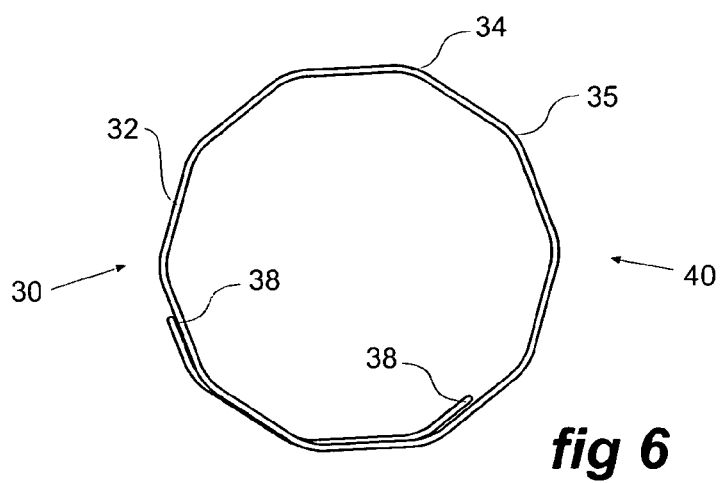
FIG. 6 shows a plan view of the embodiment of FIG. 4.

Now looking at the alternative embodiment of stent according to the present invention shown in FIGS. 4 to 6.

The stent 30 is formed from a resilient wire such as Nitinol™ wire or stainless steel and comprises a zig zag structure formed from a plurality of struts 32 with a bends 34 and 35 between each pair of struts 32. In this embodiment there are twelve struts 32, five bends 34 at one side of the zig-zag structure and six bends 35 at the other side of the zig-zag structure between them. The terminal struts 36 at each end terminate in a loop 38 which comprises at least one turn of the resilient wire and preferably one and a quarter or more turns. The use of the loops 38 prevent sharp ends from the wire stent from digging into the vasculature into which a stent graft, incorporating the self expanding stent of the present invention, is deployed. As formed the stent comprised of struts, bends and loops is in a single plane and when it is to be used it is formed into a cylindrical or polygonal body 40 as shown in FIG. 5. In the cylindrical form the struts are overlapped each other to give a two strut overlap. As there is an even number of struts then the terminal loops 38 are positioned at the same end of the cylindrical or polygonal body 20. FIG. 5 also shows that when the stent is formed into the substantially cylindrical shape then the bends 34 define a first circular shape shown by dotted line 37 and the bends 35 define a second circular shape shown by dotted line 39.

The embodiment of the stent 30 shown in FIGS. 4 to 6 has twelve struts 32 and six bends 34, 35 between them and hence when formed into cylindrical or polygonal body 40 with an overlap of two struts has a plan view in the shape of a decagon as can be seen in FIG. 3.

When assembled onto a stent graft the stent is maintained into its cylindrical or polygonal body form by being stitched to the tubular body of the graft material.

Figure 7:
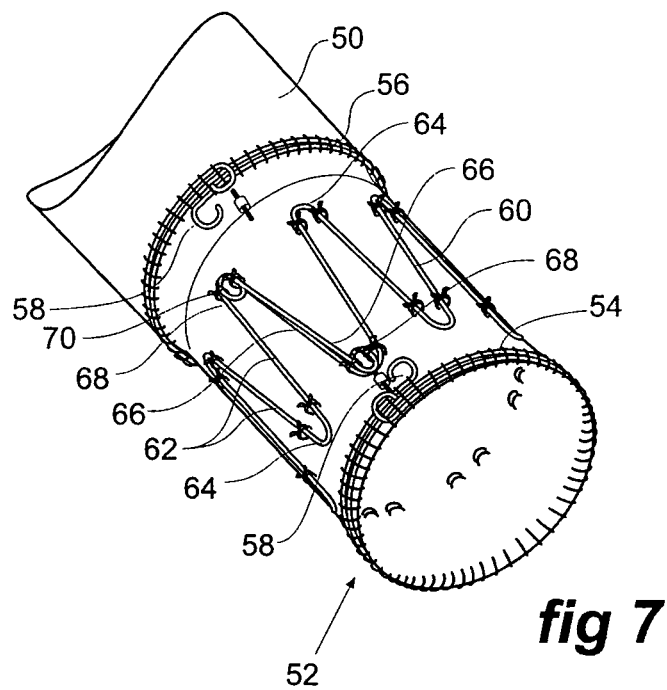
FIG. 7 shows a connection socket incorporating a stent according to the present invention.

FIG. 7 shows a connection socket of a stent graft incorporating a stent according to the present invention. The connection socket incorporating a stent of this embodiment of the invention may be for a side arm for a stent graft adapted for deployment into the common iliac artery or may be for a terminal end of a leg of a bifurcated stent graft such as a for a stent graft adapted to be deployed into the aortic bifurcation.

In this embodiment the tube 50 may be a side arm for a stent graft or may be a terminal end of a leg of a bifurcated graft. The tube 50 has a socket arrangement 52 into which may be placed a self-expanding stent, a balloon expandable stent or a composite stent or leg extension. The tube 50 has a first ring 54 stitched to its terminal end and a second ring 56 spaced apart from the first ring 54. Each ring 54 and 56 is formed from at least two turns and preferably three turns of a nitinol wire and the ends of the nitinol wire terminate in loops 58. The use of the loops 58 prevent sharp ends from the Nitinol™ wire from digging into the vasculature into which the stent graft is deployed.

Between the first ring 54 and the second ring 56 is a stent 60 according to the present invention formed from a resilient material. The stent 60 is formed from a resilient wire such as nitinol wire or stainless steel and comprises a plurality of struts 62 with bends 64 between a pair of struts 62. The terminal struts 66 at each end terminate in a loop 68 which comprises at least one turn of the resilient wire and preferably one and a quarter turns. Stitching 70 is used to both hold the stent onto the tubular body 50 as well as to maintain the stent in its cylindrical or polygonal form.

The resilient stent 60 when stitched in its cylindrical or polygonal form is made to be of a size which is at rest slightly smaller than the diameter of the tube 50 and hence when sewn on to the outside of the tube 50 using stitching 70 it provides a diameter reducing effect on the tube 50.

When a balloon expandable stent or balloon expanded covered stent is placed into the socket 52 and expanded the rings 54 and 56 provide firm locking for the balloon expanded covered stent and the resilient stent 60, which is expanded by the balloon expanded stent while it is being balloon expanded, provides a compressive effect to keep tension on the balloon expanded stent. By this means a firm connection and an improved seal can be obtained between a stent leg or arm and a bridging stent. A similar gripping effect can be obtained with the use of a self-expanding stent, a composite stent or other form of leg extension incorporation a stent according to the present invention.

In one particular embodiment the side tube may have a diameter of 8 mm and hence a circumference of 26 mm. Each of the rings may have a diameter at rest of 7 mm and the resilient stent 60 when formed into its cylindrical or polygonal form may have a diameter at rest of 6 mm. The first and second rings may be spaced apart by 10 mm and the length of the resilient stent 60 may be 6 mm. Hence there may be a gap between the rings and the resilient stent of 2 mm.

In the case of a stent graft to be deployed into the common iliac artery with the side arm adapted to extend towards the internal iliac artery the side arm may have a diameter of 8 mm and a length after the join to a main stent graft of up to 25 mm. It will be realised that for stent grafts to be deployed into the ascending or descending aorta with side arms to extend into their respective branch vessels other lengths and diameters will be applicable.

Figure 8:
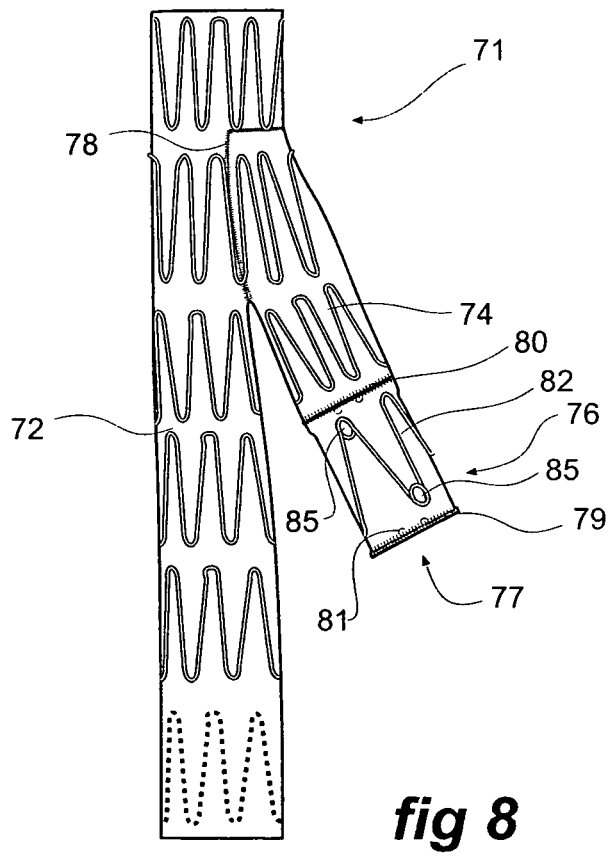
FIG. 8 shows a side branch stent graft or prosthesis of the type adapted for deployment into the iliac arteries and including a connection socket having a stent according to this invention.

FIG. 8 shows a side branch stent graft or prosthesis of the type adapted for deployment into the iliac arteries, for instance, such that a bridging stent can extend from the side arm into the internal iliac or hypogastric artery.

The stent graft 71 has a main tubular body 72 and a side arm 74. Both the main tubular body and the side arm are formed from a seamless tube of a biocompatible graft material such as Dacron. A triangular aperture is formed in the main tube and a bevel cut into the inner end of the side arm and the side arm stitched into the triangular aperture with stitching 78. The side arm has a connection socket arrangement 76 at its distal end 77. The connection socket arrangement 76 comprises a first ring 79 stitched to its terminal or distal end 77 and a second ring 80 spaced apart from the first ring 79. Each ring 79 and 80 is formed from at least two turns and preferably three turns of nitinol wire and the ends of the nitinol wire terminate in loops 81. The use of the loops 81 prevent sharp ends from the nitinol wire from digging into the vasculature into which the stent graft is deployed.

Between the first ring 79 and the second ring 80 is a stent 82 according to the present invention formed from a resilient material. The stent 82 is formed from a resilient wire such as nitinol wire or stainless steel and comprises a plurality of struts with bends between a pair of struts. In this embodiment there are seven struts and six bends between them. The terminal struts at each end terminate in a loop 85 which comprises at least one turn of the resilient wire and preferably one and a quarter turns. Stitching is used to both hold the stent onto the tubular body as well as to maintain the stent in its cylindrical or polygonal form.

When a bridging stent such as a balloon expandable stent is placed into the socket 77 as and expanded the rings 79 and 80 provide firm locking for the balloon expanded stent and the resilient stent 82 which is expanded by the balloon expanded stent while it is being balloon expanded provides a compressive effect to keep tension on the balloon expanded stent. By this means a firm connection and an improved seal can be obtained between the side arm and a bridging stent. A similar gripping effect can be obtained with the use of a bridging stent in the form of a self-expanding stent, a composite stent or other form of leg extension.

Throughout this specification various indications have been given as to the scope of but the invention is not limited to any one of these but may reside in two or more of these combined together. The examples are given for illustration only and not for limitation.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

What is claimed is:

1. A stent graft comprising:
   a tubular graft comprising a socket arrangement into which may be placed a second stent graft, the socket arrangement comprising:
   a first ring and second ring attached to the tubular graft and each comprised of a wire terminating in loops, the second ring spaced apart from the first ring;
   a stent comprising a single length of a resilient wire, the resilient wire comprising a zig zag form defined by a plurality of struts and a bend between each strut and an adjacent strut, the resilient wire comprising a first end and a second end, each end comprising a terminal strut;
   the terminal struts of the first end and the second end each terminating in a terminal loop, the terminal loops preventing the resilient wire from digging into a vasculature into which the stent graft is deployed;
   the stent being attached in a substantially cylindrical form around an outside of the tubular graft between the first ring and the second ring, the first end and the second end of the stent overlapping each other so that at least the terminal struts overlap each other along their entire length; and
   wherein the stent is sized in the cylindrical form at rest to be smaller than the diameter of the tubular graft and therefore smaller than the diameter of the first ring and second ring, thereby providing a compressive effect on the tubular graft to keep tension on the second stent graft and provide firm locking for the second stent graft.

2. A stent graft as in claim 1 comprising in the zig zag form seven struts and six bends.

3. A stent graft as in claim 1 wherein the resilient wire is selected from the group comprising stainless steel, cobalt alloys and titanium alloys.

4. A stent graft as in claim 1 wherein the terminal loops of the terminal struts comprise at least one and a quarter turns of the resilient wire.

5. A stent graft as in claim 1 wherein the struts and bends of the zig zag form of the stent are formed in a single plane, the tubular graft maintaining the stent in the cylindrical form when the stent is attached to the tubular graft.

6. A stent graft as in claim 1 wherein the stent is attached to the tubular graft by being stitched to the tubular graft.

7. A stent graft as in claim 1 wherein the struts and bends of the zig zag form of the stent are formed in a single plane, the tubular graft maintaining the stent in the cylindrical form when the stent is attached to the tubular graft, and the stent is attached to the tubular graft by being stitched to the tubular graft.

8. A stent graft as in claim 1 wherein the first ring is attached to a terminal end of the tubular graft.

9. A stent graft as in claim 8 wherein the first ring and the second ring are each formed from at least two turns of the wire.

10. A stent graft as in claim 9 wherein the tubular graft has a diameter of 8 mm and the first and the second rings have a diameter at rest of 7 mm and the stent when formed into the cylindrical form has a diameter at rest of 6 mm.

* * * * *